United States Patent [19]

Thorén

[11] 4,149,542
[45] Apr. 17, 1979

[54] ENDOCARDIAL ELECTRODE

[75] Inventor: Anders Thorén, Upsala, Sweden

[73] Assignee: Siemens Aktiengesellschaft, Berlin & Munich, Fed. Rep. of Germany

[21] Appl. No.: 763,429

[22] Filed: Jan. 28, 1977

[30] Foreign Application Priority Data

Mar. 26, 1976 [DE] Fed. Rep. of Germany ....... 2613086

[51] Int. Cl.² ............................................. A61N 1/04
[52] U.S. Cl. .................................. 128/418; 128/419 P
[58] Field of Search ...................... 128/404, 418, 419 P

[56] References Cited

U.S. PATENT DOCUMENTS

| | | | |
|---|---|---|---|
| 3,737,579 | 6/1973 | Bolduc | 128/418 |
| 3,788,329 | 1/1974 | Friedman | 128/418 |
| 3,943,936 | 3/1976 | Rasor et al. | 128/419 P |
| 3,981,309 | 9/1976 | Cannon | 128/419 P |
| 4,011,861 | 3/1977 | Enger | 128/418 X |
| 4,026,303 | 5/1977 | Babotai | 128/418 |
| 4,030,508 | 6/1977 | Thalen | 128/418 |
| 4,033,357 | 7/1977 | Helland et al. | 128/418 |

*Primary Examiner*—Lee S. Cohen
*Attorney, Agent, or Firm*—Hill, Gross, Simpson, Van Santen, Steadman, Chiara & Simpson

[57] ABSTRACT

An endocardial electrode for intracardial stimulation of a heart is comprised of an elongated electrical conductor encased within an electrical insulator with a two-component head member positioned on the insulator at the distal end of the electrode for contact with heart tissue when the electrode is operationally positioned relative to the heart. One of the head member components is in electrical contact with the elongated conductor while the other component is spaced therefrom. The component in contact with the conductor is composed of a heart-tissue compatible conductive material which exhibits a minimum heart stimulation threshold, such as carbon or the like, and the component spaced from the conductor is composed of a heart-tissue compatible material which exhibits a receptiveness for growth of heart tissue thereabout, such as platinum or the like.

12 Claims, 4 Drawing Figures

ENDOCARDIAL ELECTRODE

BACKGROUND OF THE INVENTION

1. Field of the Invention

The invention relates to medical appliances and somewhat more specifically to endocardial electrodes for intracardial stimulation of a heart.

2. Prior Art.

The art is aware of endocardial electrodes comprised of an elongated electrical conductor encased or enveloped within an electrical insulator and having an electrode head or tip on the distal end of such conductor for transmitting stimulating impulses to the heart pursuant to the controlled application of an electrical current to the conductor. In endocardial electrodes of this type, the electrode head or tip is composed of a heart compatible material which is not receptive to heart tissue growth thereabout so that such electrode tip merely loosely rests on the stimulable heart muscle. Such an endocardial electrode is rather easily removed or accidentally displaced from the stimulable muscle so that the current density on such muscle is reduced and presents a danger to the heart patient.

U.S. Pat. No. 3,953,864 suggests an endocardial electrode having a somewhat cage-shaped electrode head with spaces between the external periphery-defining edges thereof for tissue growth after positioning of such electrode in the heart. After tissue growth, this type of electrode cannot be removed or accidentally dislodged from the stimulable heart muscle. However, this electrode is disadvantageous in that a comparatively high stimulation threshold is present because of the non-stimulable cellular and/or connective tissue growths forming about the electrode head. A further disadvantage of this electrode is the relatively complicated construction thereof.

SUMMARY OF THE INVENTION

The invention provides an endocardial electrode of the type above described which avoids the prior art drawbacks.

In accordance with the principles of the invention, an electrocardial electrode is provided with a two-component head member, one of which is composed of a compatible electrically conductive material which exhibits a minimum heart stimulation threshold and the other of which is composed of a compatible material which exhibits a receptiveness for heart tissue growth.

Somewhat more specifically, endocardial electrodes constructed in accordance with the principles of the invention are provided with a two-component head member, one of which is in electrical contact with the elongated conductor of the electrode while the other component is spaced from such conductor and the component in electrical contact with the conductor is composed of a heart tissue compatible conductive material having a minimum heart stimulation threshold, such as carbon or the like, while the head component spaced from the conductor is composed of a heart tissue compatible material which exhibits a receptiveness for growth of heart tissue thereabout, such as a metal, a ceramic or a synthetic material.

In certain preferred embodiments of the invention, the head component in electrical contact with the conductor is positioned at the distal tip of the electrode and the component spaced from the conductor is positioned adjacent or proximate to the distal tip. The head component composed of the tissue growth receptive material may have a plurality of peripheral openings therein, such as grooves or pores having an average opening diameter of about 50 to 500 μm for the ingrowth of heart tissue into such openings.

DESCRIPTION OF THE PREFERRED EMBODIMENTS

The invention provides endocardial electrodes having a minimum heart stimulation threshold and being receptive to good heart tissue growth onto such endocardial electrodes.

In accordance with the principles of the invention, an endocardial electrode is comprised of an elongated electrical conductor enveloped or encased within an electrical insulator and having an electrode head member located at the distal end of said conductor for transmitting stimulating impulses to the heart pursuant to a controllably applied electrical current to said conductor. The head member is comprised of two components which are positioned adjacent or proximately to one another and on the insulator. One of the head member components is positioned in electrical contact with the elongated conductor while the other head member component is spaced from the conductor. The component in contact with the conductor is composed of a heart tissue compatible electrically conductive material which exhibits a minimum heart stimulation threshold, such as carbon and the like. Materials exhibiting a minimum heart stimulation threshold are not overly receptive for tissue growth thereabout so that no increase in the stimulation threshold occurs after the placement of components composed of such a material in areas of tissue growth, such as a heart. The head member component spaced from the elongated electrode is composed of a compatible material which exhibits a receptiveness to good heart tissue growth about such a component. Such tissue growth receptive material is selected from the group consisting of metals, ceramics or synthetic materials, for example, such as platinum, tantalum, titanium, aluminum oxide, polyethylene, silicone rubber and the like.

Figure 1:
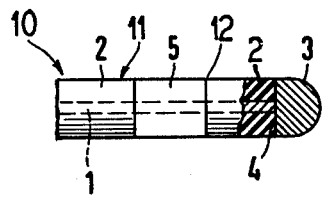
FIG. 1 is a fragmentary elevational view, with parts broken away and in cross-section as well as parts shown in phantom, of an embodiment of an endocardial electrode constructed in accordance with the principles of the invention.

Referring now to the drawings wherein like elements have like reference numerals, FIG. 1 illustrates an embodiment 10 of an endocardial electrode 11. The endocardial electrode 11 includes an elongated electrical conductor 1 which is enveloped or encased with an electrical insulator 2 and includes an electrode head member 12 at the distal end of the electrode. The head member 12 is of generally cylindrical construction and is comprised of two components, one being a tip component 3 and the other being an annular side component 5.

The head member tip component 3 may be of a somewhat hemispherical shape, being rounded-off at the free end thereof. However, the tip component may also have other shapes as desired, for example, a cylindrical shape or the like. In the embodiment shown at FIG. 1, the tip component 3 is electrically connected at the rear end 4 thereof with the electrical conductor 1. The tip component 3 is composed of an electrically conductive material which is compatible with heart tissue and which exhibits a minimum heart stimulation threshold, such as carbon or the like. The stimulation threshold for a heart is defined as the least amount of energy required for initiating a heartbeat. A component composed of a material exhibiting a minimum heart stimulation threshold is not receptive to tissue growth so that when an endocardial electrode having the construction shown at FIG. 1 is inserted in a heart, no stimulable tissue grows about tip 3 and the stimulation threshold remains low.

The head member side component 5 is arranged or positioned in the proximity of the tip component 3. In the embodiment shown at FIG. 1, the side component 5 functions to retain the endocardial electrode in proper position within the heart. In the form shown, head component 5 is a ring-shaped member and is spaced from the electrical conductor 1 by the insulator 2. Further, in this embodiment, the head component 5 is also spaced a distance from the tip component 3 and the space between these components is filled with the insulator 2. The side component 5 is composed of a compatible material which exhibits a receptiveness for heart tissue growth and is selected from the group consisting of metals, ceramics and synthetic materials. Preferred metals include platinum, titanium and tantalum. Preferred ceramic materials include aluminum oxide. Preferred synthetic materials include silicone rubber, such as available under the trade name "Silastic" and plastics, such polyethylene.

The side component 5 may be provided with openings in the peripheral surface thereof, such as pores or grooves having an average opening diameter ranging from about 50 μm to about 500 μm and preferably being in the range of about 100 to 200 μm. Such surface openings facilitate the anchoring of the endocardial electrode as the heart tissue grows into such peripheral openings. Manufacturing processes for producing such porous components are known and may comprise, for example, sintering select powder particles having a suitable average particle size, for example, an average diameter of about 100 to 500 μm. Slots or grooves may be provided by assembling the component 5 from a plurality of partial ring-like discs or the like onto an appropriately sized cylindrical body so that empty spaces remain between the ring-like discs into which the tissue may grow. Other forms of construction are, of course, possible.

Figure 2:
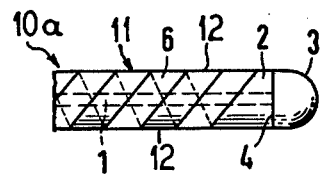
FIGS. 2-4 are somewhat similar views of further embodiments of endocardial electrodes constructed in accordance with the principles of the invention.

In embodiment 10a shown at FIG. 2, a side component 6 having a helical construction replaces component 5 of embodiment 10 discussed in conjunction with FIG. 1.

Figure 3:

In embodiment 10b shown at FIG. 3, the side component 5 is positioned in direct contact with a porous tip component 3a and an electrical connection is provided between the conductor 1 and the component 5. In this embodiment, tip component 3a is spaced by insulator 2 from the conductor 1. The tip component 3a is provided with a plurality of slots or grooves 3b on the peripheral surface thereof for the ingrowth of tissue.

Figure 4:
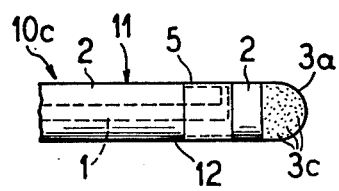

In embodiment 10c shown at FIG. 4, the conductor 1 is terminated short of a porous tip component 3a and is in electrical contact with only side component 5. The tip component 3a is shown as having a plurality of pores 3c on the peripheral surface thereof for the ingrowth of tissue.

Accordingly, the invention encompasses endocardial electrode embodiments wherein the head component or tip 3a is composed of a compatible material which is receptive to good tissue growth thereabout and the head member side component or annular member 5 is composed of tissue-compatible electrically conductive material which exhibits a minimum heart-stimulation threshold. In embodiments where component 5 is the signal or energy-transmitting element, it must, of course, be operationally connected to the conductor 1. Such connection is readily accomplished, for example, by the construction shown at FIG. 3 where the conductor 1 is provided with a radially extending flange for contact with component 5. Thus, endocardial electrodes constructed in accordance with the principles of the invention are characterized by an electrode head with exhibits a minimum heart stimulation threshold and, simultaneously, is adapted for a secure anchorment of the electrode within the heart by tissue growing about a portion thereof.

As is apparent from the foregoing specification, the present invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the hereto-appended claims.

I claim as my invention:

1. In an endocardial electrode for intercardial stimulation of a heart, comprising an elongated electrical conductor enveloped by an electrical insulator and having a distal end for contact with a heart and a proximal end for contact with a controllably applied electrical current, said conductor having an electrode head member located at the distal end of said conductor and in electrical communication therewith for transmitting stimulating electrical impulses to the heart pursuant to the controllably applied electrical current provided to the conductor, the improvement comprising wherein:

said electrode head member is comprised of a first and a second component, said first component being in electrical contact with said conductor and being composed of carbon which is tissue-compatible and exhibits a minimum heart-tissue stimulation threshold and said second component being spaced from said first component as well as from said conductor and electrically insulated from each, said second component being positioned toward the proximal end of said conductor relative to said first component, said second component being composed of platinum which exhibits a ready receptiveness to heart-tissue growth.

2. An endocardial electrode as defined in claim 1 wherein said head member components are separated from one another by said electrical insulator.

3. An endocardial electrode as defined in claim 1 wherein said head member component exhibiting a receptiveness to heart tissue growth is a ring-shaped member mounted about said elongated conductor and spaced therefrom by said insulator.

4. An endocardial electrode as defined in claim 3 wherein said ring-shaped member is of a helical construction.

5. In an endocardial electrode for intercardial stimulation of a heart, comprising an elongated electrical conductor enveloped by an electrical insulator and having a distal end for contact with a heart and a proximal end for contact with a controllably applied electrical current, said conductor having an electrode head member located at the distal end of said conductor and in electrical communication therewith for transmitting stimulating electrical impulses to the heart pursuant to the controllably applied electrical current provided to the conductor, the improvement comprising wherein:

said electrode head member is comprised of a first and a second component, said first component being in electrical contact with said conductor and being composed of carbon which is tissue-compatible and exhibits a minimum heart-tissue stimulation threshold and said second component being spaced from said first component as well as from said conductor and electrically insulated from each, said second component being positioned toward the proximal end of said conductor relative to said first component, said second component being composed of a ceramic material which exhibits a ready receptiveness to heart-tissue growth.

6. An endocardial electrode as defined in claim 5 wherein said head member components are separated from one another by said electrical insulator.

7. An endocardial electrode as defined in claim 5 wherein said head member component exhibiting a receptiveness to heart-tissue growth is a ring-shaped member mounted about said elongated conductor and spaced therefrom by said insulator.

8. An endocardial electrode as defined in claim 7 wherein said ring-shaped member is of a helical construction.

9. In an endocardial electrode for intercardial stimulation of a heart, comprising an elongated electrical conductor enveloped by an electrical insulator and having a distal end for contacting a heart and a proximal end for contact with a controllably applied electrical current, said conductor having an electrode head member located at the distal end of said conductor and in electrical communication therewith for transmitting stimulating electrical impulses to the heart pursuant to the controllably applied electrical current provided to the conductor, the improvement comprising wherein:

said electrode head member is comprised of a first and a second component, said first component being in electrical contact with said conductor and being composed of carbon which is tissue-compatible and exhibits a minimum heart-tissue stimulation threshold and said second component being spaced from said first component as well as from said conductor and electrically insulated from each, said second component being positioned toward the proximal end of said conductor relative to said first component, said second component being composed of a metal which exhibits a ready receptiveness to heart-tissue growth.

10. An endocardial electrode as defined in claim 9 wherein said head member components are separated from one another by said electrical insulator.

11. An endocardial electrode as defined in claim 9 wherein said head member component exhibiting a receptiveness to heart-tissue growth is a ring-shaped member mounted about said elongated conductor and spaced therefrom by said insulator.

12. An endocardial electrode as defined in claim 11 wherein said ring-shaped member is of a helical construction.

* * * * *